United States Patent [19]
Chang et al.

[11] Patent Number: 4,786,509
[45] Date of Patent: Nov. 22, 1988

[54] DRY SUSTAINED RELEASE THEOPHYLLINE ORAL FORMULATION

[75] Inventors: Richard Chang, Miramar; Robert P. Giannini, Plantation; Charles Hsaio, Cooper City, all of Fla.

[73] Assignee: Schering Corporation, Kenilworth, N.J.

[21] Appl. No.: 51,095

[22] Filed: May 18, 1987

[51] Int. Cl.$^4$ .............................................. A61K 9/16
[52] U.S. Cl. .................................. 424/490; 424/491; 424/494; 514/263; 514/962; 514/964
[58] Field of Search ............... 424/459, 462, 494, 497, 424/490, 491; 514/263, 962, 964

[56] References Cited

U.S. PATENT DOCUMENTS

| | | | |
|---|---|---|---|
| 3,835,221 | 9/1974 | Fulberth et al. | 424/20 |
| 4,083,949 | 4/1978 | Benedikt | 424/19 |
| 4,587,118 | 5/1986 | Hsiao | 424/459 |
| 4,692,337 | 9/1987 | Ukigayo et al. | 424/469 |

OTHER PUBLICATIONS

Pedersen et al., Pediatrics, vol. 74, No. 4, pp. 534–538, (1984).

*Primary Examiner*—Michael Lusignan
*Attorney, Agent, or Firm*—Gerald S. Rosen; Thomas D. Hoffman; Stephen I. Miller

[57] ABSTRACT

A sustained release theophylline containing oral dosage formulation comprising theophylline containing micropellets coated with from about 0.5% to about 2% by weight of a pharmaceutically acceptable water-insoluble film former, preferably ethyl cellulose and having first order release. The formulation is an improvement over theophylline containing micropellets coated with two film formers which have zero order release. The oral dosage formulation has superior non-fasting release and absorption characteristics when compared to the zero order release formulation.

6 Claims, No Drawings

DRY SUSTAINED RELEASE THEOPHYLLINE ORAL FORMULATION

BACKGROUND OF THE INVENTION

A zero order release theophylline product, THEO-DUR SPRINKLE ™, by Key Pharmaceuticals, has received widespread acceptance in the marketplace and among the medical profession as a bronchodilator. The product is a formulation of dry sustained release oral dosage micropellets in a capsule which includes upper and lower connectible parts which are easily separable from each other. The micropellets provide sustained release of theoohylline when taken by a patient and are comprised of inner seeds coated with theophylline which in turn is coated with a mixture of ethylcellulose and hydroxypropylcellulose. The oral dosage formulation is administered by separatinq the upper and lower parts of the capsule and placing the micropellets on food, the food is then eaten.

The preparation of the product is described in U.S. Pat. No. 4,587,118.

Pedersen et al, PEDIATRICS, 74 (4), 534, (Oct. 4, 1984) discovered, in a clinical study involving asthmatic children using THEO-DUR SPRINKLE theophylline micropellets, that the bioavailability and absorption pattern of the theophylline were satisfactory under fasting conditions but both absorption pattern and bioavailability were severely adversely affected by concomitant food intake. A dela y in absorption was found and the bioavailability was reduced from 91% (fasting) to 44% ($P<0.001$). They concluded that the erratic absorption of theophylline after food intake complicates safe therapy with the preparation. This is a serious problem since the dosage form was developed for use with food by those having difficulty swallowing tablets or capsules, e.g. the elderly and children.

There is thus a need for a slow-release theophylline sprinkle composition which provides satisfactory bioavailability and absorption pattern when taken orally with food or shortly after ingestion of food, i.e., under non-fasting conditions.

SUMMARY OF THE INVENTION

The oral sustained release theophylline formulation of the present invention provides a means to administer theophylline in a micropellet formulation which enables patients to receive the correct therapeutic blood level of theophylline under either fasting or nonfasting conditions.

This invention is based on the discovery that a first order release theophylline product provides the desired bronchodilator effect when administered with food or shortly thereafter. This is accomplished by providing micropellets containing a coating of about 0.5% to 2.0% by weight, preferably about 1.5% by weight of a pharmaceutically acceptable water insoluble film former, e.g. ethylcellulose, based on the weight of the micropellets. The coating composition is 100% film former and the thickness of the coating is a function of the amount film former present. The coating does not contain any plasticizers or water-soluble additives.

The micropellets of this invention are utilized in an easily openable capsule containing a sufficient amount of the micropellets to provide a dosage unit of theophylline. The dosage unit administered to a patient is determined by the attending clinician taking into consideration the age, size and condition of the patient as well as the severity of the disease. Thus, for example, with children aged 8 to 12 years old, a dose of about 9 to 11 mg/kg is utilized.

The compositions of this invention display first order release and have equivalent in vivo results to the prior art zero order release formulation when administered to a fasting subject. However, the compositions of this invention maintain their in vivo performance when administered with food or shortly after food is ingested by the patient, whereas the prior art compositions have reduced effectiveness under such conditions.

DETAILED DESCRIPTION OF THE INVENTION

The micropellets of this invention are prepared by coating sugar seeds with a mixture of theophylline and polyvinylpyrrolidone as described in U.S. Pat. No. 4,587,118. The resulting seeds are then coated with a pharmaceutically acceptable water-insoluble film former, e.g. ethylcellulose, from a solvent system such as ethylacetate, methylene chloride/methanol or chloroform/methanol. Ethyl acetate is the preferred solvent system.

Capsules filled with the micropellets of this invention are those which are easily opened. The micropellets are poured out of the opened capsule onto a food substance for oral administration. Any number of micropellets can be present within the capsule provided their numbers in relation to their size and surface area results in providing therapeutic blood levels of the theophylline. It is desirable that the micropellets are sufficiently small such that their presence within the mouth is not easily discernible, but sufficiently large so that they can be seen when placed on food. There are typically less than 1000 micropellets within each capsule, preferably about 800–900 micropellets which is sufficient to provide a 100 milligram dose of theophylline per capsule.

As described in U.S. Pat. No. 4,587,118 and incorporated by reference herein, the micropellets are made by coating theophylline in micronized form onto a sugar seed having a 60–80 mesh size (U.S. Sieve Series). The theophylline is coated onto the sugar seed by first combining it with a water soluble film former such as polyethylene glycol or polyvinylpyrrolidone. Preferred is polyvinylpyrrolidone having a molecular weight of from about 30,000 to about 50,000 with about 40,000 preferred.

The resulting theophylline coated sugar seeds are then coated with a pharmaceutically acceptable waterinsoluble film former such as ethylcellulose, cellulose acetate butyrate or cellulose triacetate, with ethyl cellulose preferred. This coating enables first order release of the theophylline. The averagediameter of each of the finished micropellets is about 0.5 to 0.7 mm, preferably about 0.6 mm.

The dissolution rate is dependent on the amount of film former on a weight basis compared to the total weight of the micropellets and is influenced by the solvent system from which the film former is applied as well as the concentration of the film former in the solvent system.

When using the preferred ethyl cellulose, it is preferred to apply from about 0.5% to 2.0% by weight ethyl cellulose from an ethyl acetate solvent containing about 1% to 5% (w/v) ethyl cellulose. This results in a coating significantly thinner than the one made according to U.S. Pat. No. 4,587,118. A preferred method is to apply about 1% to 1.5% by weight ethyl cellulose from a 1% to 3% (w/v) ethyl acetate solution. This provides a coating with a sufficient amount of channels to enable the theophylline to be released as desired. The ethyl cellulose preferred for use in this invention contains 2.25–2.28 ethoxyl groups per anhydroglucose unit.

Contrary to the observation made in U.S. Pat. No. 4,587,118 at col. 4, lines 62–68 and col. 5, lines 1 and 2 that ethyl cellulose used as the sole coating is unsatisfactory, when using the amounts of pharmaceutically acceptable water-insoluble film former as recited herein, the first order release of theophylline is equivalent to the zero order release in vivo under fasting conditions. Furthermore, there is no change under non-fasting conditions of in vivo performance of the first order release formulation of this invention when compared to fasting conditions.

The following examples illustrate the invention.

EXAMPLE 1

A typical formulation for the products of this invention is as follows

| INGREDIENTS | % By Weight |
| --- | --- |
| Theophylline Anhydrous USP (Pulverized) | 75.4 |
| Sucrose NF (60–80 Mesh, U.S. Sieve) | 4.0 |
| Povidone USP (Kollidon 30) | 19.0 |
| Ethocel N-10 (Dow ethylcellulose) | 1.6 |
| Total | 100.0 |

METHOD OF PREPARATION (a) Using a Glatt GCPC-5 fluid bed granulating apparatus sold by Glatt Air Techniques, Inc., of Raritan, N.J. equipped with a 6" Wurster air suspension coating column, 3.2 kilograms polyvinylpyrrolidone, molecular weight 40,000 (Kollidon 30) were dissolved in 32 liters of isopropanol and 12.8 kilograms of micronized theophylline were dispersed therein. 4.0 kilograms of sugar, 60/80 mesh, was placed in the Wurster air suspension coating column. After the air suspension system was in operation with the sugar, the dispersed theophylline was sprayed into the column with the inlet air having a temperature of 60° C., the spray pressure at 4 bars, and the spray rate being 100 ml/min. After completion of the above procedure, operation of the Wurster column was stopped, and the product reserved as "theophylline pellets, Active I".

(b) A second 3.2 kilogram batch of polyvinylpyrrolidone, molecular weight 40,000 (Kollidon 30) was dissolved in 32 liters of isopropanol, and dispersed into the resultant mixture was 12.8 kilograms of micronized theophylline. 4.0 kilograms of "theophylline pellets, Active I" were then charged into the same Wurster column under the same conditions of temperature and pressure, and at the same rate as in step (a). The second batch having the theophylline dispersed therein was then charged into the Wurster column to further build up the coating. The Wurster column was emptied and the product labelled "Theophylline pellets, Active II".

(c) A coating mixture of 1280 ml of chloroform and 320 ml of methanol was prepared. 16 gms of ethylcellulose (Ethocel N-10, Dow) was dispersed therein. Into the Wurster column was charged 984 gm of "theophylline pellets, Active II" which were then coated with the coating mixture under conditions of 40° C., spray pressure 1 bar and spray rate 15 ml/min. The line was rinsed with 10 ml chloroform and the pellets were dried for approximately twenty minutes and recovered.

The pellets were then screened through a #18 U.S. Sieve mesh screen.

The resultant coated pellets were small white micropellets which may be placed into capsules containing the desired dosage unit.

EXAMPLE 2

Steps (a) and (b) of Example 1 were followed to obtain the product labelled "Theophylline pellets, Active II.".

The final coated product containing an ethylcellulose coating level of 0.8% was prepared using a Uni-Glatt apparatus equipped with a Wurster air suspension coating column (Glatt Air Techniques, Inc., Raritan, N.J.)

A coating mixture of 1280 ml of methylene chloride and 320 ml of methanol was prepared. 3.2 gms of ethylcellulose [Ethocel N-10, Dow) was dispersed therein. Into the Wurster column was charged 492 gms of "theophylline pellets, Active II" which were then coated with the coating mixture under conditions of 40° C., spray pressure 1 bar, and spray rate 10 ml/min. The line was rinsed with methylene chloride and the pellets were dried for approximately twenty minutes and recovered to give a product of 99.2% by weight theophylline active pellets and 0.8% by weight ethylcellulose coating.

EXAMPLE 3

The procedure of Example 2 was followed except, instead of 0.2% ethylcellulose concentration in the methylene chloride:methanol (4:1) solvent, there was 1%. The resulting product had the same level of ethylcellulose coating as in Example 2 (0.8%) and was composed of 99.2% by weight theophylline active pellets and 0.8% by weight ethylcellulose coating.

EXAMPLE 4

The procedure of Example 2 was followed except, instead of 0.2% ethylcellulose concentration in the methylene chloride:methanol solvent there was 5%. The resulting product had the same level of ethylcellulose coating as in Example 2 (0.8%) and was composed of 99.2% by weight theophylline active pellets and 0.8% by weight ethylcellulose coating.

EXAMPLE 5

The procedure of Example 1 was followed wherein the concentration of ethylcellulose in the chloroform:methanol (4:1) solvent was 1.0%, using a coating level of 0.8% by weight of ethylcellulose on the theophylline active pellets to give a product with 99.2% by weight theophylline active pellets and 0.8% by weight ethylcellulose coating.

EXAMPLE 6

The procedure of Example 1 was followed except the coating level of ethylcellulose was 1.2% by weight, giving a product with 98.4% by weight theophylline active pellets and 1.2% by weight of ethylcellulose coating.

EXAMPLE 7

The procedure of Example 1 was followed except the coating level of ethylcellulose was 1.4% by weight, giving a product with 98.6% by weight theophylline active pellets and 1.2% by weight of ethylcellulose coating.

The batch sizes of Examples 2, 3 and 4 were 0.8 kg. The batch sizes of Examples 1, 5, 6 and 7 were 1.0 kg.

EXAMPLE 8

Using a Glatt GCPC-5 coating apparatus equipped with a Wurster Column, a coating mixture of 7100 ml ethyl acetate with 213 gms. ethylcellulose dispersed therein was prepared. 15,000 gms of "theophylline pellets Active II" as prepared in Example 1, steps (a) and (b) was charged into the Wurster column. The theophylline pellets were then coated with the coating mixture under conditions of 40° C., spray pressure 2.5 bar and spray rate 70 ml/minute to yield a product with 1.4% by weight ethylcelluose coating and 98.6% by weight theophylline active pellets.

EXAMPLE 9

The procedure of Example 8 was followed except the coating level of ethylcellulose was 1% by weight giving a product with 99% by weight theophylline active pellets and 1% by weight ethylcellulose coating.

EXAMPLE 10

The procedure of Example 8 was followed except the level of ethylcellulose coating was 1.6% by weight giving a product with 98.4% by weight theophylline active pellets an 1.6% by weight ethylcellulose coating.

EXAMPLE 11 AND 12

The procedure of Example 8 was followed to give in each of Examples 11 and 12 a product with 98.6% by weight theophylline active coating and 1.4% by weight ethylcellulose coating.

By following the procedures of Example 1 but using appropriate amounts of ingredients and solvents, the micropellets were produced having the following coating level of water-insoluble film forming polymer, preferably ethyl cellulose—0.5%, 0.8%, 1.2%, 1.4%, 1.6%.

The resulting products were tested to determine their dissolution, i.e. % theophylline released over a finite period of time utilizing the U.S.P. XX dissolution procedure using simulated intestinal fluid as the dissolution medium. The following results were obtained:

TABLE 1

| | DISSOLUTION DATA FOR THEOPHYLLINE MICROPELLETS USING ETHYLCELLULOSE ALONE AS THE COATING MATERIAL | | | | | | | | |
|---|---|---|---|---|---|---|---|---|---|
| EXAMPLE # | SPRAY SOLVENT | POLYMER CONC. IN SOLVENT (%) | ETHYLCELLULOSE COATING LEVEL (%) | DISSOLUTION DATA (% RELEASED) HOURS | | | | | |
| | | | | 1 | 2 | 4 | 6 | 8 | 10 |
| 1 | Chloroform:Methanol (4:1) | 1 | 1.6 | 23 | 41 | 62 | 76 | 85 | 90 |
| 2 | Methylene Chloride:Methanol (4:1) | 0.2 | 0.8 | 74 | 80 | 84 | 87 | 88 | 91 |
| 3 | Methylene Chloride:Methanol (4:1) | 1 | 0.8 | 34 | 51 | 75 | 88 | 95 | 100 |
| 4 | Methylene Chloride:Methanol (4:1) | 5 | 0.8 | 59 | 74 | 85 | 91 | 94 | 97 |
| 5 | Chloroform:Methanol (4:1) | 1 | 0.8 | 81 | 97 | 100 | | | |
| 6 | Chloroform:Methanol (4:1) | 1 | 1.2 | 46 | 68 | 89 | 97 | 102 | |
| 7 | Chloroform:Methanol (4:1) | 1 | 1.4 | 32 | 53 | 76 | 88 | 95 | 100 |
| 8 | Ethyl Acetate | 3 | 1.4 | 21 | 34 | 50 | 62 | 70 | 75 |
| 9 | Ethyl Acetate | 3 | 1.0 | 31 | 49 | 71 | 83 | 91 | 95 |
| 10 | Ethyl Acetate | 3 | 1.6 | 13 | 22 | 36 | 47 | 56 | 63 |
| 11 | Ethyl Acetate | 3 | 1.4 | 17 | 25 | 42 | 53 | 62 | 69 |
| 12 | Ethyl Acetate | 3 | 1.4 | 14 | 25 | 43 | 55 | 64 | 70 |

The data in the Table show that the coating level, the concentration of the polymer in the solvents used to apply the coating and the identity of the solvents affects the release characteristics of the coated micropellets. In addition, the data shows that using a polymer concentration of 3% produces results less consistent than lower concentrations.

Data developed in tests conducted to determine the extent and rate of theophylline absorption from the micropellets of this invention under fasting and nonfasting conditions show that food did not deteriously affect the extent and rate of theophylline absorption and the resulting plasma concentration was not significantly different than the fasting state.

We claim:

1. A first order sustained release theophylline composition comprising theophylline-containing micropellets having on the outside surface thereof a coating consisting of a pharmaceutically acceptable water-insoluble single film former present in an amount of from about 0.5% to about 2.0% by weight based on the weight of said micropellets.

2. A composition of claim 1 wherein said coating is ethyl cellulose.

3. A composition of claim 2 wherein the ethyl cellulose coating is about 1.5% by weight.

4. A first-order sustained release unit dosage form of theophylline comprising an easily openable capsule having therein a plurality of theophylline-containing micropellets, the amount of micropellets in said capsule comprising a dosage unit of theophylline, wherein each of said micropellets have a coating thereon of from about 0.5% to about 2.0% by weight based on the weight of said micropellets of a single pharmaceutically acceptable water-insoluble film former.

5. A unit dosage form of claim 4 wherein the film former is ethyl cellulose.

6. A unit dosage form of claim 5 wherein the amount of ethylcellulose coating is about 1.5% by weight.

* * * * *